US009757490B2

(12) United States Patent
Santini et al.

(10) Patent No.: US 9,757,490 B2
(45) Date of Patent: Sep. 12, 2017

(54) MEMBRANE DEVICE FOR THE RELEASE OF VOLATILE COMPOSITIONS

(71) Applicant: Takasago International Corporation, Tokyo (JP)

(72) Inventors: Thomas F. Santini, Doylestown, PA (US); Anthony R. Budraitis, Hoboken, NJ (US)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 84 days.

(21) Appl. No.: 13/943,515

(22) Filed: Jul. 16, 2013

(65) Prior Publication Data
US 2014/0048614 A1    Feb. 20, 2014

Related U.S. Application Data

(60) Provisional application No. 61/762,180, filed on Jul. 16, 2012, provisional application No. 61/838,747, filed on Jun. 24, 2013.

(51) Int. Cl.
*A24F 25/00* (2006.01)
*A61L 9/12* (2006.01)
(Continued)

(52) U.S. Cl.
CPC .............. *A61L 9/12* (2013.01); *A61L 9/122* (2013.01); *B32B 7/12* (2013.01); *B32B 15/08* (2013.01);
(Continued)

(58) Field of Classification Search
CPC ...... A61L 9/12; A61L 9/122; A61L 2209/131; B32B 27/306; B32B 15/08; B32B 27/32;
(Continued)

(56) References Cited

U.S. PATENT DOCUMENTS 4,145,001 A * 3/1979 Weyenberg ............... A61L 9/12
156/289
4,283,011 A * 8/1981 Spector ................. A01M 29/12
239/36
(Continued)

FOREIGN PATENT DOCUMENTS

DE     298 09 384     12/1998
EP     0 081 791      6/1983

OTHER PUBLICATIONS

International Search Report and Written Opinion for PCT/US2013/050695, dated Jan. 10, 2014.
(Continued)

*Primary Examiner* — Arthur O Hall
*Assistant Examiner* — Joel Zhou
(74) *Attorney, Agent, or Firm* — Baker Botts L.L.P.

(57) ABSTRACT

A membrane device is intended for the release of volatile compositions. The membrane device includes one or more membrane layers which are permeable to the volatile composition and which are positioned within a vapor impermeable package such as package formed by an upper and lower vapor impermeable panel. The upper vapor impermeable panel includes a window that allows access to the membrane layer for activation of the membrane device. The membrane device can also include decorative portions for aesthetic appeal.

20 Claims, 12 Drawing Sheets

(51) Int. Cl.
  B32B 7/12    (2006.01)
  B32B 15/08   (2006.01)
  B32B 15/20   (2006.01)
  B32B 27/08   (2006.01)
  B32B 27/30   (2006.01)
  B32B 27/32   (2006.01)
  B32B 27/34   (2006.01)
  A61L 9/03    (2006.01)
  A61L 9/04    (2006.01)

(52) U.S. Cl.
  CPC .............. *B32B 15/20* (2013.01); *B32B 27/08* (2013.01); *B32B 27/304* (2013.01); *B32B 27/306* (2013.01); *B32B 27/32* (2013.01); *B32B 27/34* (2013.01); *A61L 9/03* (2013.01); *A61L 9/048* (2013.01); *A61L 2209/131* (2013.01); *B32B 2270/00* (2013.01); *B32B 2307/724* (2013.01); *B32B 2307/7246* (2013.01); *B32B 2307/7248* (2013.01); *B32B 2439/46* (2013.01)

(58) Field of Classification Search
  CPC ......... B32B 27/304; B32B 15/20; B32B 7/12; B32B 27/08; B32B 27/34; B32B 2307/7246; B32B 2270/00; B32B 2307/7248; B32B 2307/724
  USPC ......................................... 239/34, 36, 42, 58
  See application file for complete search history.

(56) References Cited

U.S. PATENT DOCUMENTS

| | | | |
|---|---|---|---|
| 5,782,409 A * | 7/1998 | Paul .......................... | A61L 9/12 239/56 |
| 5,798,385 A | 8/1998 | Marin | |
| 7,926,735 B1 * | 4/2011 | Mobley ..................... | A61L 9/04 206/449 |
| 2003/0168521 A1* | 9/2003 | Skalitzky et al. .............. | 239/57 |
| 2005/0148479 A1* | 7/2005 | Barthel et al. ................. | 510/101 |
| 2009/0130047 A1* | 5/2009 | Weiss et al. .................. | 424/76.2 |
| 2009/0302128 A1* | 12/2009 | Zobele ................ | A01M 1/2044 239/59 |
| 2011/0243628 A1* | 10/2011 | MacLean .................. | B32B 3/14 400/76 |

OTHER PUBLICATIONS

Partial European Search Report for EP Application No. EP 13176740.2, dated Nov. 12, 2013.

* cited by examiner

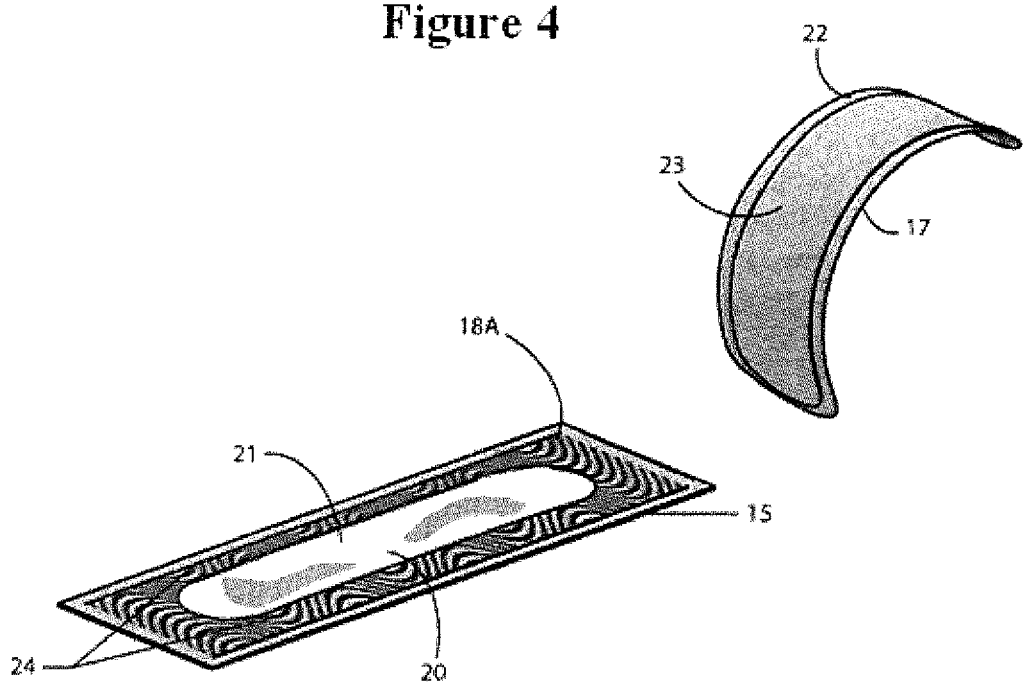

DETAIL D
SCALE 5 : 1

MEMBRANE DEVICE FOR THE RELEASE OF VOLATILE COMPOSITIONS

CROSS-REFERENCE TO RELATED APPLICATIONS

This application claims priority to U.S. Provisional Application Ser. No. 61/672,180 filed on Jul. 16, 2012 and U.S. Provisional Application Ser. No. 61/838,747 filed on Jun. 24, 2013, each of which is incorporated herein by reference in their entireties and for all purposes.

FIELD OF THE INVENTION

The presently disclosed subject matter relates to membrane devices for the sustained release of volatile fragrances, deodorizing compositions, or other volatile compositions over prolonged periods of time.

BACKGROUND OF THE INVENTION

A variety of air freshening forms exist in the marketplace that offer the consumer an array of performance options. Such air freshening foil is include aerosols, gels, energy driven units, porous carriers, and membrane devices.

Aerosol sprays offer immediate fragrance awareness upon activation, but dissipate quickly over time. In addition, aerosol sprays represent a costly method of fragrance delivery once the expenses associated with the aerosol container, valve, propellant, and formula, and the manufacturing costs, are taken into consideration.

Water-based gels have traditionally represented one of the least expensive cost options for fragrance delivery due to the large concentration of water in these formulas and formulations. However, a fragrance dispersed in an aqueous gel and thickened with a hydrocolloid generally results in large sized units with a typically short functional life of about 2-3 weeks. Gels are frequently marketed in sizes ranging from 150 grams to 250 grams where the co-evaporation of water with fragrance results in a shrunken residue that is considered highly unattractive.

Power-assisted units, whether they are based on the use of heat, a fan, or both to assist in fragrance dispersion, have been proposed. The energy assisted fragrance dispersion contributes to a greater fragrance awareness. However, such units come at an economic cost that makes these units expensive to manufacture and operate.

Porous carriers are described in U.S. Pat. No. 7,926,735 to Mobley et al. In Mobley, the porous carrier, such as a paperboard card, is impregnated with a fragrance compound for diffusion. However, when fragrance is absorbed directly onto a substrate such as paper, the fragrance release is inordinately high when the paper is newly exposed and subsequently drops dramatically as time passes.

Membrane devices have become appreciated for their lightweight construction and generally smaller size. Membrane devices typically are constructed with a release membrane covering the full expanse of a shallow tray, which contains the fluid contents to be dispensed. Such membrane devices, however, offer no platform for graphic design applications. Therefore, it is necessary to utilize a separate housing to contain the membrane cartridge. Such housing may enable a surface for design.

U.S. Pat. No. 4,145,001, to Weyenberg et al., describes a package having an absorbent pad located under a permeable layer that is uniformly but weakly bonded to an upper barrier layer. In order to activate the package of Weyenberg, a user completely removes the upper barrier layer from the permeable layer. However, the complete removal of the upper barrier layer does not allow the package to provide a visual or decorative enhancement when in use. Moreover, because the entire upper barrier is removed to expose the entire permeable layer to the ambient air, the options for adjusting the delivery rate are limited. For a given fragrance composition and package material, the delivery rate for the package of Weyenberg can be adjusted only by changing the thickness of the permeable layer or changing the size of the package. However, each of these options would require modifications to the manufacturing machinery such as the permeable layer forming machinery.

There remains a need in the art to provide a small-sized, easily deployed, and disposable membrane air freshener, which has design potential, is economical to fabricate, and which will provide a pleasing fragrance experience over the functional life of the device.

SUMMARY OF THE INVENTION

It is an object of the presently disclosed subject matter to create a flexible multi-layered membrane device including a permeable membrane suitable for the release of volatile compositions such as fragrances, insecticides, deodorants, medicants, and the like.

In accordance with one embodiment of the disclosed subject matter, a membrane device for release of a volatile composition includes a lower barrier panel comprising an impermeable material, a volatile composition sealed between the lower barrier panel and a membrane layer, a membrane layer comprising a permeable material and being sealed between the lower barrier panel and an upper barrier panel, an upper barrier panel comprising an impermeable material and including a window, and a removable segment covering the window. The removable segment can comprise an impermeable material and a tear strip handle. The tear strip handle can be bonded to the removable segment on an adhesive-coated side thereof.

The volatile composition can include a fragrance, a liquid, a gel, or a rheologically modified liquid. The permeable material can include a copolymer film of polyethylene and ethylene vinyl acetate. The upper barrier panel can include multiple independent layers. For example, the upper barrier panel can include one or more of a sealing layer, a layer of polyethylene terephthalate, an outer layer printed with a design element, and a vapor impermeable layer. The membrane layer can be sealed between the lower barrier panel and the upper barrier panel by one of a heat seal and a sonic weld.

The window can be a die-cut window or a kiss-cut window. The device can further include an adhesive placement strip attached to the lower barrier panel.

In accordance with another embodiment of the disclosed subject matter, the membrane device includes an outer pouch and an inner pouch. The outer pouch includes a barrier layer comprising an impermeable material and further comprising a window, and a removable segment covering the window. The removable segment can comprise an impermeable material and a tear strip handle. The tear strip handle can be bonded to the removable segment on an adhesive-coated side thereof. The inner pouch comprises a permeable material and can be sealed inside the outer pouch. A volatile composition can be sealed within the inner pouch. The inner pouch can be completely constructed from a permeable material. Alternatively, the inner pouch can include both permeable and impermeable portions. The inner pouch and/or outer pouch can be formed using a single sheet construction and sealed using a fin seal, or formed from two sheets of material that are sealed together using, e.g., a four seam configuration.

The volatile composition can include a fragrance, a liquid, a gel, or a rheologically modified liquid. The permeable material can include a copolymer film of polyethylene and ethylene vinyl acetate. The barrier layer can include multiple independent layers. For example, the barrier layer can include one or more of a sealing layer, a layer of polyethylene terephthalate, an outer layer printed with a design element, and a vapor impermeable layer.

The window can be a die-cut window or a kiss-cut window. The device can further include an adhesive placement strip attached to the outer pouch.

A method for releasing a volatile composition in accordance with the disclosed subject matter can include providing a membrane device including a lower barrier panel comprising an impermeable material, a volatile composition sealed between the lower barrier panel and a membrane layer, the membrane layer comprising a permeable material and being sealed between the lower barrier panel and an upper barrier panel, the upper barrier panel comprising an impermeable material and further comprising a window, and a removable segment covering the window. The removable segment can comprise an impermeable material and a tear strip handle. The tear strip handle can be bonded to the removable segment on an adhesive-coated side thereof. The method can further include removing the tear strip.

The method can further include placing the membrane device using an adhesive placement strip. The membrane device can be placed, for example, beneath a surface. In another embodiment, the method can include placing the membrane device in a laundry dryer. The laundry dryer can then be turned on. In accordance with yet another embodiment, the membrane device can be placed in a dispersal unit. A fan or a heating element of the dispersal unit can then be activated.

A method for releasing a volatile composition in accordance with another embodiment of the disclosed subject matter includes providing a membrane device comprising an outer pouch and an inner pouch. The outer pouch can include a barrier layer comprising an impermeable material and further comprising a window, a removable segment covering the window, and a removable segment covering the window. The removable segment can comprise an impermeable material and a tear strip handle. The tear strip handle can be bonded to the removable segment on an adhesive-coated side thereof. The inner pouch comprises a permeable material and can be sealed inside the outer pouch. A volatile composition can be sealed within the inner pouch. The method further includes removing the removable segment.

The method can further include placing the membrane device using an adhesive placement strip. The membrane device can be placed, for example, beneath a surface. In another embodiment, the method can include placing the membrane device in a laundry dryer. The laundry dryer can then be turned on. In accordance with yet another embodiment, the membrane device can be placed in a dispersal unit. A fan or heating element of the dispersal unit can then be activated.

A method for manufacturing a membrane device in accordance with one embodiment of the disclosed subject matter can include partially sealing a membrane layer between a lower barrier panel comprising an impermeable material and an upper barrier panel comprising an impermeable material, the membrane layer comprising a permeable material, filling a space between the lower barrier panel and the membrane layer with a volatile composition, sealing the volatile composition between the lower barrier panel and the membrane layer, and cutting a window in the upper barrier panel.

The method can include filling the space between the lower barrier panel and the membrane layer using a mechanical filler. Sealing can include, for example, heat sealing or sonic welding. Cutting can include, for example, die cutting or kiss cutting.

A method for manufacturing a membrane device in accordance with another embodiment of the disclosed subject matter can include partially creating an inner pouch comprising a permeable material, filling the inner pouch with a volatile composition, sealing the volatile composition within the pouch, sealing the inner pouch within an outer pouch comprising a barrier layer comprising an impermeable material, and cutting a window in the barrier layer.

The method can include filling the inner pouch using a mechanical filler. Sealing can include, for example, heat sealing or sonic welding. Cutting can include, for example, die cutting or kiss cutting.

It is to be understood that both the foregoing general description and the following detailed description are exemplary and are intended to provide further explanation of the disclosed subject matter.

The accompanying drawings, which are incorporated in and constitute part of this specification, are included to illustrate and provide a further understanding of the disclosed subject matter. Together with the written description, the drawings serve to explain the principles of the disclosed subject matter.

BRIEF DESCRIPTION OF THE DRAWINGS

FIG. 2 highlights the multi-laminate construction of the barrier panels of the membrane device, and includes the vapor releasing membrane. FIG. 2 also illustrates the relative orientation of each of the materials used in the fabrication of the membrane device.

In FIG. 3A, the package is partially opened with the sealing tear strip about to be completely free of contact with the upper barrier layer.

FIG. 4 illustrates another exterior perspective view of the membrane device of FIG. 3A. In FIG. 4, the sealing tear strip is completely removed from the package and the vapor releasing membrane is fully exposed.

FIG. 6B shows the appearance of the dispersal unit as it would appear in an operational mode.

In FIG. 8, the package is partially opened with the sealing tear strip about halfway to being completely free of contact with the upper barrier layer.

In FIG. 8A, the sealing tear strip is completely removed from the package and the vapor releasing membrane is fully exposed.

DETAILED DESCRIPTION

Reference will now be made in detail to various embodiments of the disclosed subject matter, non-limiting examples of which are illustrated in the accompanying drawings. The device presented herein generally is intended for releasing a volatile composition into the surrounding environment. In accordance with the disclosed subject matter, a device containing a volatile composition is provided. The device includes a volatile medium, a vapor releasing membrane, a lower barrier panel, an upper barrier panel including a window, and a tear strip including a removable segment and a tear strip handle. The lower barrier panel, upper barrier panel, and removable segment each comprise one or more sublayers. Such sublayers can comprise an impermeable material. The vapor releasing membrane can include a permeable material. The tear strip handle can be bonded to the removable segment on an adhesive-coated side thereof to form a tear strip. The tear strip can be adhesively connected to the upper barrier layer.

For purpose of explanation and illustration, and not limitation, an exemplary embodiment of the package in accordance with the application is shown in FIGS. 1 through 4.

Figure 1A:
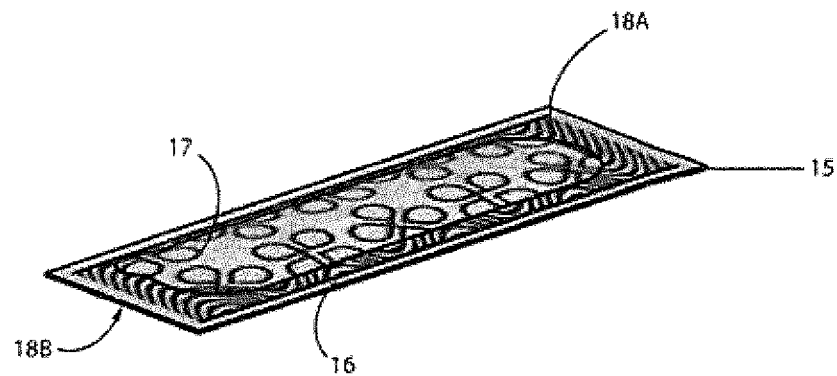
FIG. 1A illustrates an exterior perspective view of a filled, sealed and printed membrane device in accordance with one embodiment of the disclosed subject matter.

The membrane device (15) shown in FIG. 1A is in an unactivated (i.e., unopened) state. The membrane device (15) has a generally rectangular shape and a substantially planar orientation, although a wide variety of designs can be used without departing from the scope of the disclosed subject matter.

Figure 1B:
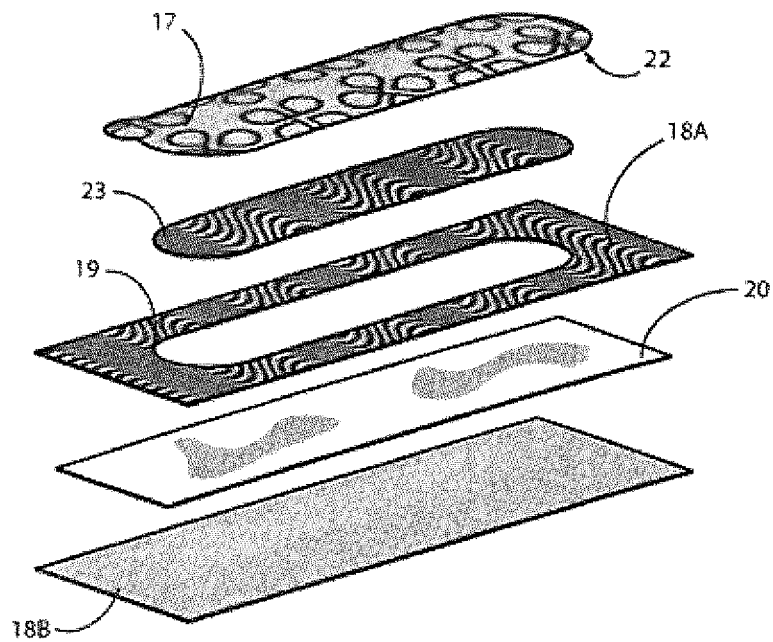
FIG. 1B illustrates an exploded view of the components of the membrane device of FIG. 1A. The membrane device includes a design printed on the available printable surfaces.

An exploded view of the membrane device of FIG. 1A, which illustrates the components for the membrane device as well as the relative orientation of each component in relation to the others, is shown in FIG. 1B. The membrane device generally includes a vapor releasing membrane (20), a lower barrier panel (18B), an upper barrier panel (18A) with a window (19), a removable segment (23), and a tear strip handle (17). The membrane device also contains a volatile composition initially located in a fill zone between the vapor releasing membrane (20) and the lower barrier panel (18B).

Volatile Medium

The volatile composition, in general, can be any material that, upon activation of the membrane device, is capable of being diffused into the surrounding environment. As such, a wide variety of volatile compositions can be used within the scope of the disclosed subject matter. The volatile compositions can be, for purposes of explanation and not limitation, a fragrance, an insecticide, a malodor counteractant, a medicant, or the like. The volatile composition can be in a number of different form including but not limited to, for example, a liquid or a gel composition.

In accordance with one embodiment of the disclosed subject matter, the volatile medium can be a rheologically modified liquid. Rheological additives that can be used to modify the viscosity of a liquid such as a fragrance oil can include colloidal silica, modified clays, polymer additives such as ethyl cellulose, or elastomeric compositions such as styrene block copolymers sold under the trade name Kraton™.

The amount of the volatile composition contained within the membrane device can be adjusted to suit the needs of a particular application such that the membrane device provides, e.g., an odor intensity and length of life, which supports the intended purpose of the device. For example, in one embodiment, the amount of the volatile composition is selected such that the membrane device is capable of delivering an olfactive experience for approximately 4 to approximately 6 weeks or approximately 3 to approximately 8 weeks. Alternatively, the amount of volatile composition can be selected such that the membrane device is capable of delivering an olfactive experience for at least about 3 weeks, at least about 4 weeks, at least about 5 weeks, at least about 6 weeks, or at least about 7 weeks. The use of concentrated compositions that are readily permeable through the vapor releasing membrane can provide for a long term continuous use of the membrane device and can allow the manufacture of smaller devices, thereby reducing the overall material cost per unit. In accordance with various embodiments of the disclosed subject matter, the amount of volatile composition in the membrane device can be between about 1 gram and about 7 grams, between about 2 grams and about 5 grams, or between about 3 grams and about 4 grams. For example, the membrane device can include at least about 1 gram, at least about 2 grams, at least about 3 grams, at least about 4 grams, about 1.5 grams, about 2 grams, about 2.5 grams, about 3 grams, about 4 grams, or about 4.5 grams of the volatile composition. In a particular embodiment, the amount of volatile medium can be about 3.5 grams.

Figure 2:
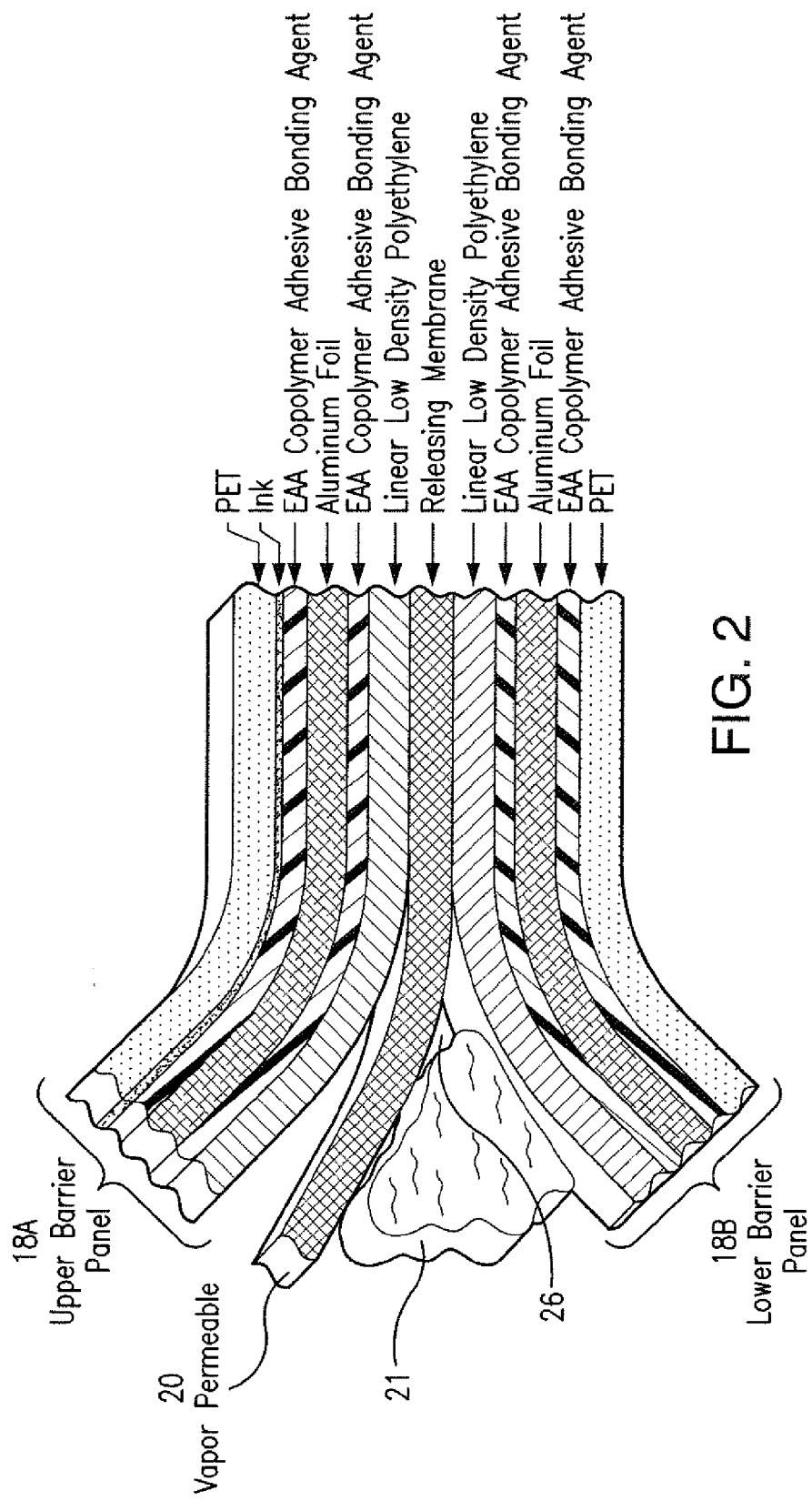
FIG. 2 illustrates an expanded cross-sectional view of a membrane device in accordance with one embodiment of the disclose subject matter.

An exemplary embodiment of a portion of a membrane device in accordance with the disclosed subject matter is shown in FIG. 2. The volatile composition (21) is located in a fill zone (26) formed in the voided volume between a lower barrier panel (18B) and a vapor releasing membrane (20). The flexible construction of the membrane device (15) allows for easy expansion for receipt of the volatile composition when the membrane device is oriented in an upright position.

Vapor Releasing Membrane

A vapor releasing membrane (20) is permeable to the volatile composition (21) such that when the membrane device (15) is activated, the volatile composition (21) can be diffused through the vapor releasing membrane (20) and into the surrounding environment. The vapor releasing membrane (20) can be sealably engaged between the upper barrier panel and the lower barrier panel, and thus is not visible when the membrane is in the unactivated state shown in FIG. 1A. The vapor releasing membrane (20) controls the release of vapor, and in one embodiment can provide a uniform or substantially uniform delivery over the functional life of the product. Releasing membranes offer the advantages of a rate controlling diffusion process through the vapor releasing membrane as contrasted with direct evaporation or evaporation from an inert substance such as paper blotter. The vapor releasing membrane (20) can be, for example, made of copolymer film of polyethylene and ethylene vinyl acetate. However, other materials such as polymeric compositions permeable to the volatile composition (21) can also be used. For purposes of explanation and not limitation, the vapor releasing membrane (20) can also be constructed using low, medium, and high density polyethylene, polypropylene, cellulose acetate, co-polymers of polyethylene and ethylene-vinyl acetate, co-polymers of polypropylene and ethylene-vinyl acetate, polyvinyl chloride, ethylene-vinyl acetate (EVA), polysulfone, polyether sulfone, polytetrafluoroethylene, and nylon. Surlyn® polymeric film (DuPont de Nemours) and micro porous polypropylene membranes such as Celgard® (commercially marketed by the Celgard Corporation) and Teslin® (commercially marketed by PPG Industries) can also be used as the material for creating the vapor releasing membrane in accordance with the disclosed subject matter. The composition of the vapor releasing membrane (20) can be selected based on the nature of the volatile composition (21) being released and the release rate necessary to deliver suitable functionality. As such, a wide variety of materials can be used to construct the vapor releasing membrane (20) without departing from the scope of the disclosed subject matter as long as the vapor releasing membrane (20) is permeable to the volatile composition (21) contained in the membrane device (15). The vapor releasing membrane can have a caliper of from about 1 mil to about 5 mil, from about 2 mil to about 4 mil, and from about 2 mil to about 3 mil. For example, the vapor releasing membrane can have a caliper of at least about 1 mil, at least about 2 mils, at least about 3 mils, at least about four mils, and at least about 5 mils. In a particular embodiment, the caliper is about 2 mil.

The term "about" or "approximately," as used herein, means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to +/−20%, preferably up to +/−10%, more preferably up to +/−5%, and more preferably still up to +/−1-1% of a given value. Alternatively, particularly with respect to biological systems or processes, the term can mean within an order of magnitude, preferably within 5-fold, and more preferably within 2-fold, of a value.

The vapor releasing membrane can also be evaluated for suitability. For example, when in contact with the volatile composition, the outside surface of the vapor releasing membrane can be a material that remains dry to the touch. Selection of such a material can afford the most flexible placement and diminishes problems with the membrane device causing unwanted damage to target locations, including but not limited to, household surfaces in areas of likely use such as kitchen counters or fine furniture.

The vapor permeable membrane (20) can be designed so that the rate of vapor dispersion into the surrounding atmosphere suits the intended purpose of the membrane device (15). For example, if the membrane device dispenses fragrance, the membrane device (15) should be designed to provide a sufficient concentration of fragrance aroma chemicals into the surrounding atmosphere to create an indoor odor awareness. Two aspects of membrane design are the membrane composition and membrane thickness. Once the membrane material is selected, a membrane thickness can be selected to provide an acceptable effective release rate.

In accordance with various embodiments of the disclosed subject matter, the membrane thickness can be between about 0.0005 inches to about 0.0050 inches, between about 0.0015 inches to about 0.0040 inches, or between about 0.0020 inches and about 0.0030 inches. For example, the membrane thickness can be less than about 0.0050 inches, less than about 0.0040 inches, less than about 0.0030 inches, less than about 0.0025 inches, about 0.0040 inches, about 0.0030 inches, or about 0.0020 inches. In a particular embodiment, the membrane thickness can be about 0.0035 inches grams. In accordance with another embodiment, the membrane thickness can be about 0.0025 inches.

Barrier Panels

With further reference to FIGS. 1B and 2, the membrane device (15) can include an upper barrier panel (18A) and a lower barrier panel (18B). As shown in FIG. 2, the membrane device (15) can include multiple layers which compose the upper and lower barrier panels (18A, 18B) of the membrane device (15). The upper and lower vapor impermeable panels (18A & 18B) can share the same construction or may be designed with different configurations.

The barrier panels of FIG. 2 can be formed by a laminating process in which a plurality of separate, distinct, and independent layers are bonded together to form a single roll stock. In particular, the barrier panels of FIG. 2 include five layers. Typically, the roll stock will have a finished thickness of between about 3 and about 5 mils, although the size can be varied depending on the needs of a particular application. A wide variety of materials can be used in constructing the barrier panels. For example, the materials for the construction of the barrier panels can be selected based upon the barrier properties the materials exhibit in order to contain the volatile composition of the package without allowing unwanted escape of, e.g., aroma chemicals. The material of the outside layer of the bather panels can also be selected to offer a suitable surface for high speed printing. The layers of the barrier panels can be held together by means of an adhesive bonding agent. The adhesive bonding agent can be, for example, an ethylene acrylic acid (EAA) co-polymer adhesive, ethylene-ethyl acrylate, or ethylene-methyl acrylate. In various embodiments, the adhesive bonding agent can be applied as a hot melt to a thickness of between about 7 pounds per ream and about 14 pounds per ream, between about 8 pounds per ream and about 12 pounds per ream, between about 7 pounds per ream and about 12 pounds per ream, or between about 9 pounds per ream and about 11 pounds per ream. In a particular embodiment, the adhesive bonding agent can be applied to a thickness of about 10 pounds per ream. In another embodiment, layers of the barrier panels can be held together by a layer of low density polyethylene which is laminated using a heat setting process to tie the layers above and below the polyethylene together. The low density polyethylene can be applied to a thickness of between about 6 pounds per ream and about 10 pounds per ream, between about 5 pounds per ream and about 11 pounds per ream, or between about 7 pounds per ream and 9 pounds per ream.

With further reference to FIG. 2, the innermost layer of the barrier panels is the sealing layer. The sealing material can be selected based on the ability of the material to be seamed in a heat sealing process so that when the two innermost layers of the barrier panels (18A, 18B) are in contact, a thermal weld can be used to seam the two together. The sealing layer of the upper barrier panel (18A) can be sealed to the sealing layer of the lower barrier panel (18B) with the vapor releasing membrane (20) and the volatile composition (21) between the sealing layers to form the membrane device (15). When sealed together by a seaming process such as, e.g., a heat sealing process, the sealing layers of the upper and lower barrier panels should prevent the volatile composition from leaking from the membrane device. The sealing layer can be constructed using, for example, a linear low density polyethylene (LLDPE), low, medium, and high density polyethylene, polypropylene, blends of ethyl vinyl acetate (EVA) and LLPDE, and blends of ethylene methyl acrylate (EMA) and LLDPE. However, other materials can be used without departing from the scope of the disclosed subject matter. The sealing layer can have a thickness of between about 1 mil and about 5 mils, between about 1.5 mils and about 4 mils, or between about 2 mils and about 3 mils. In a particular embodiment, the sealing layer can be about 2.5 mil thick.

The outer layer of each barrier panel (18A & 18B) in FIG. 2 can provide a surface for providing a design element. The outer layer can also offer barrier properties to the volatile contents of the membrane device. As such, the outer layer can be selected based on one or both of the properties of being easily printed and being an effective barrier for use with volatile compositions such as fragrance and other commonly used aroma chemicals. The outer layer can be constructed using, for example, 48 gauge (0.00048 in.) polyethylene terephthalate (PET) film. However, other materials can be used without departing from the scope of the disclosed subject matter. For purposes of explanation and not limitation, the outer layer can be constructed from low, medium, or high density polyethylene, polypropylene, polyvinyl chloride, ethylene vinyl acetate (EVA), nylon, poly(ethylene terephthalate), and poly (vinylidene chloride).

The outer layer can be decorated using a reverse printing method in which the underside of an outer layer of the barrier panel (e.g., a clear PET) is printed and the adhesive (e.g., the tie down layer of EAA co-polymer lamination adhesive) is pigmented in white so as to make the printing visible. Other colors can also be used as long as the layer can be printed and the resulting design is readable. Reverse printing has the added advantage of keeping the printing separated from the volatile composition, as the combination of the volatile compositions and the printing inks is likely to have a tendency to have a negative effect on the design element. Other methods for printing the outer layer of the barrier panels can also be used without departing from the scope of the disclosed subject matter.

With further reference to FIG. 2, the middle layer of the barrier panels (18A & 18B) is the vapor impermeable layer. The vapor impermeable material can be selected based on the ability of the material to prevent the vapor composition from diffusing through the vapor impermeable layer into the surrounding environment. The middle layer of the barrier panels can be constructed using, for example, a thin metal foil such as aluminum foil, polyacrylonitrile (e.g., as commercially marketed under the trade name Barex™ by INEOS), ethylene vinyl alcohol copolymer, metalized poly (ethylene terephthalate) (MET-PET), metalized oriented polypropylene (MET-OPP), polytetrafluoroethylene (e.g., as commercially marketed under the trade name Teflon™ by Du Pont), and the like. The middle layer can have a thickness of between about 0.00010 and about 0.00050 inches, between about 0.00020 and about 0.00045 inches, or between about 0.00025 and about 0.00035 inches. In a particular embodiment, the middle layer can have a thickness of about 0.00035 inches. The middle layer (e.g., a layer of metal foil) can be located between the outer layer (e.g., a layer of PET) and the sealing layer (e.g., a layer of LLDPE) and adhesively laminated to each of these layers by means of the adhesive bonding agent (e.g., EAA co-polymer lamination adhesive).

The vapor permeable membrane (20) is placed between the upper and lower barrier panels (18A, 18B) prior to sealing. The upper and lower barrier layers are then sealed together by sealing the sealing layer of the upper barrier panel to the sealing layer of the lower barrier panel. These layers can be sealed together, for example, by heat sealing. Other sealing methods such as sonic welding can also be used for their ordinary purpose as known in the art. With further reference to FIG. 1, the perimeter seam (16) around all sides of the package indicates that the membrane device has been fully sealed and serves to enclose the volatile composition contained within the membrane device.

The membrane device (15) can be formed into its desired size and shape when the perimeter seam is formed on three sides leaving one short side open. The membrane device (15) can then be filled with a volatile composition. One method of filling utilizes a mechanical filler, which opens the membrane device. A filling head will dose the requisite fill into the fill zone (26), and the membrane device will then be sealed. However, any filling and sealing options can be used for their intended purpose as known in the art.

With further reference to FIG. 1B, the upper barrier panel (18A) includes a window. The upper barrier panel can, for example, be die cut to provide a die cut window (19) in the upper barrier panel (18A). In general, the membrane device (15) is provided with a vapor impermeable material covering the window (19) and can be activated by exposing the window (19) to the surrounding environment. The size of the window (and therefore the area of the exposed surface of the vapor releasing membrane) can be adjusted to provide different release rates depending upon the performance objective established for the membrane device.

Figure 7:
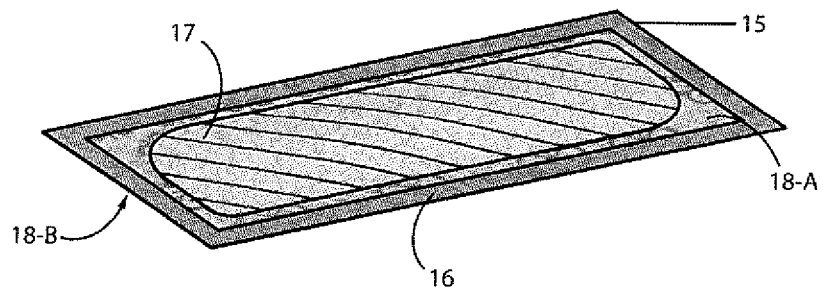
FIG. 7 illustrates an exterior perspective view of a filled, sealed and printed membrane device in accordance with one embodiment of the disclosed subject matter.
Figure 7A:
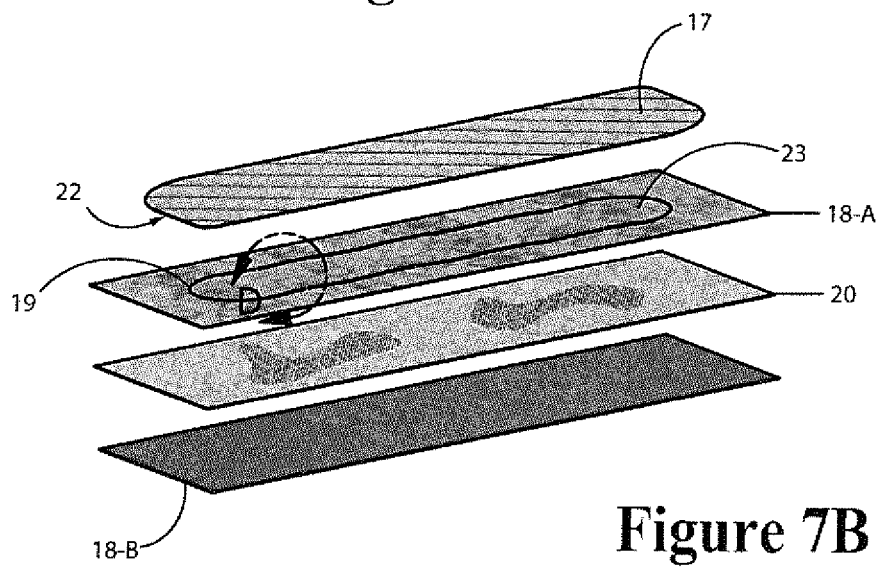
FIG. 7A illustrates an exploded view of the components of the membrane device of FIG. 7. The membrane device includes a design printed on the available printable surfaces.
Figure 7B:
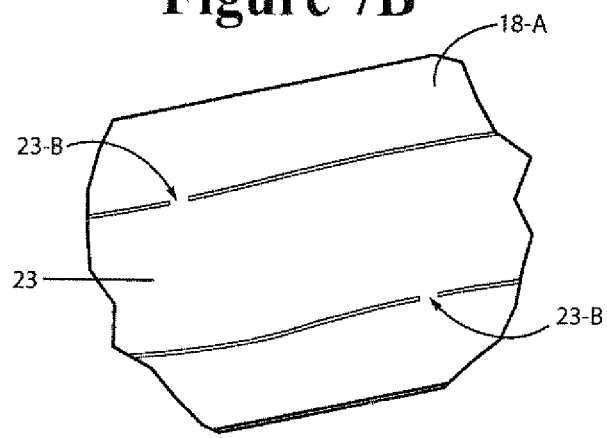
FIG. 7B illustrates an expanded perspective of the die cut window of the membrane device shown in FIG. 7.
Figure 8:
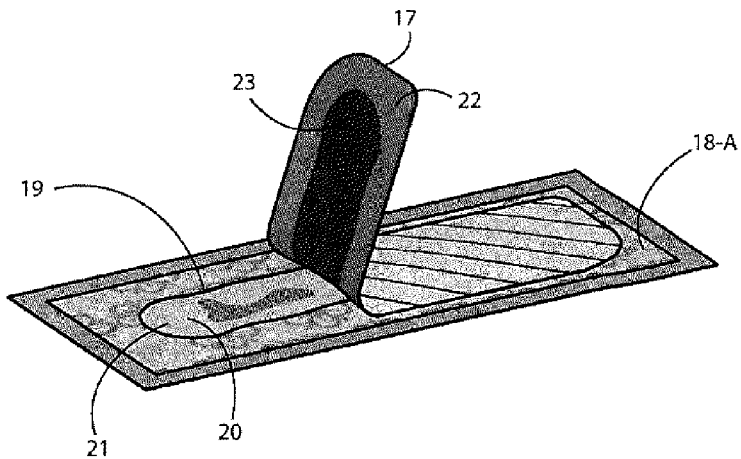
FIG. 8 illustrates an exterior perspective view of a membrane device in accordance with one embodiment of the disclosed subject matter.
Figure 8A:
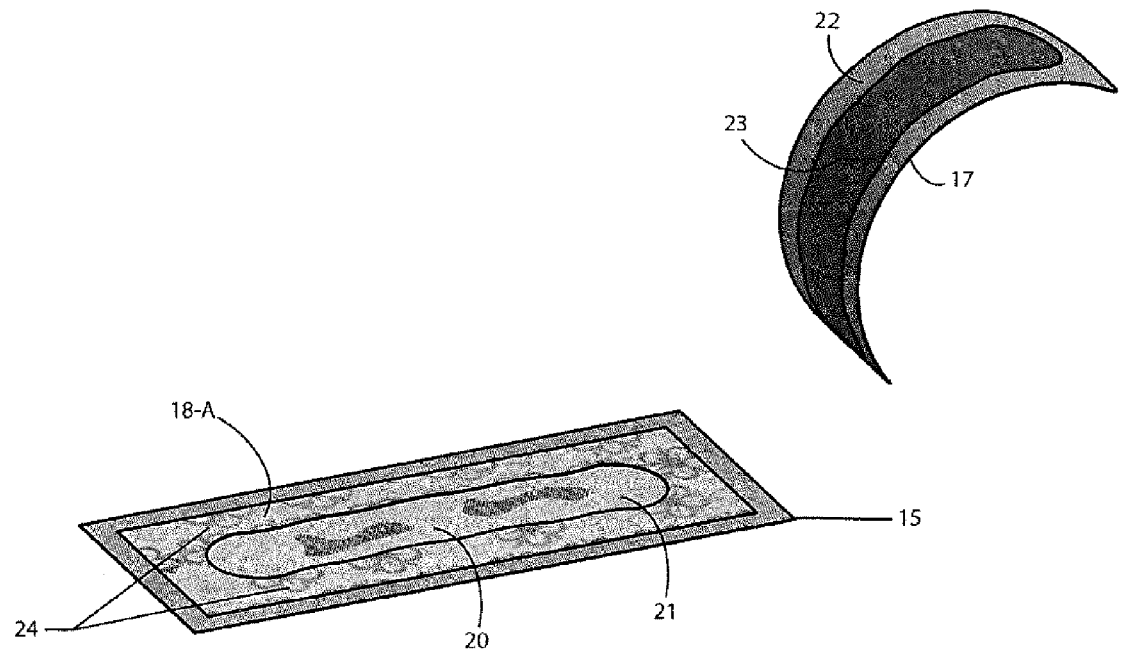
FIG. 8A illustrates another exterior perspective view of the membrane device of FIG. 8.

With reference to FIG. 7B, a die cut segment (23) can be formed in the upper barrier panel (18A) by using a die cutting process. Although the die cut segment (23) is almost completely separated from the upper barrier panel (18A), at least one tab (23B) remains intact to keep the die cut segment (23) in place. A tear strip can subsequently be attached to the die cut segment (23) and extend onto the upper barrier panel (18A) in order to create a closure to the unit and prevent unwanted loss of the active contents prior to activation.

Alternatively, a kiss-cut can be used to form the window. A kiss-cut can deliver an exact cut (e.g., with an accuracy of approximately 3 microns) using a very controlled process of pressure in combination with a rotary die. Using a kiss cut, a thin amount of the upper barrier panel remains uncut, providing for a continuous barrier between the membrane and the adhesive peel strip. The uncut portion of the film is sufficiently thin that it can be torn when the shearing force used for removal of the sealing tear strip is applied. The amount of residual film that is left uncut is determined by the depth of the kiss-cut, and can be varied to suit particular applications. Kiss-cuts may be especially useful where the volatile medium has the potential for unwanted interaction with the adhesive of the tearing strip (e.g., where the volatile medium is an acetate or a hydrocarbon).

Figure 3A:
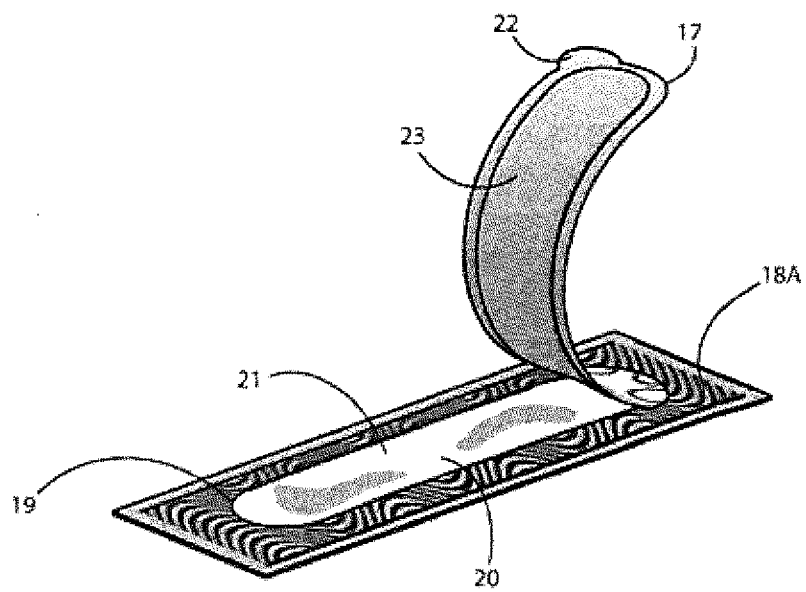
FIG. 3A illustrates an exterior perspective view of a membrane device in accordance with one embodiment of the disclosed subject matter.
Figure 3B:
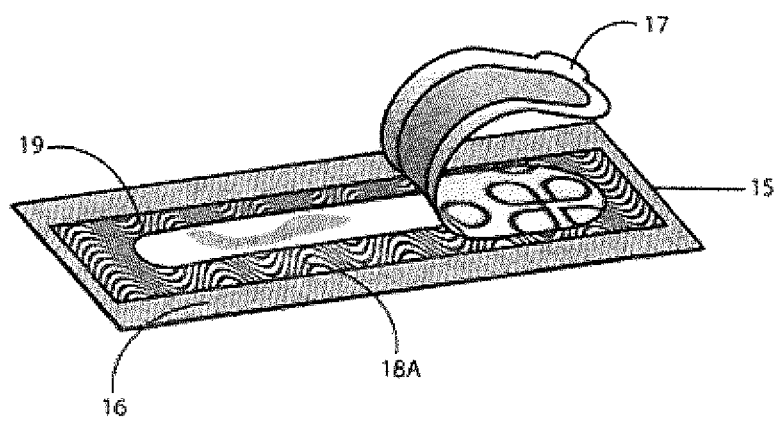
FIG. 3B illustrates an exterior perspective view of a membrane device having the same outside dimensions as the membrane device illustrated in FIG. 3A, but with a substantially smaller window than that shown in FIG. 3A.

FIGS. 3A and 3B illustrate two embodiments of a membrane device in accordance with the disclosed subject matter. FIGS. 3A and 3B both show an adhesive tear strip that is partially separated from the upper barrier panel (18A), exposing the window (19) in the upper barrier panel (18A). The membrane device of FIG. 3B is similar to the membrane device of FIG. 3B, but has a smaller window (19). The release rate of the membrane device (15) can be influenced by, among other things, membrane composition, membrane thickness, and the area of the exposed surface of the vapor releasing membrane. Therefore, the rate of vapor transmission of the membrane device depicted FIG. 3A would be higher than the rate of vapor transmission of the membrane device depicted in FIG. 3B assuming that all other parameters (e.g., membrane thickness, membrane composition, identity of the volatile composition) are the same. The difference in vapor transmission is attributable to the variance in the exposed surface. The ability to easily vary the size of the window allows the membrane device to be adapted for a variety of applications as the window can be made either larger or smaller to accommodate desired differences in release rate without the necessity of changing the overall package dimensions. This can also prevent, or at least minimize, changes to the manufacturing line.

In accordance with various embodiments of the disclosed subject matter, the area of the exposed membrane surface can be between about 0.5 in$^2$ and about 5 in$^2$, between about 1 in$^2$ and about 4 in$^2$, or between about 2 in$^2$ and 3 in$^2$. For example, the area of the exposed membrane surface can be about 0.5 in$^2$, about 1 in$^2$, about 1.5 in$^2$, about 2 in$^2$, about 2.5 in$^2$, about 3 in$^2$, or about 4 in$^2$. In a particular embodiment, the area of the exposed membrane surface can be about 2.33 in$^2$.

The fill requirements (i.e., the amount of the volatile composition that should be contained in the membrane device) can differ for various embodiments of the disclosed subject matter based on the needs of a particular application (including parameters such as the identity of the volatile composition). Thus, the amount of the volatile composition that is loaded into the membrane device (15) can be adjusted so that the exposed membrane surface in combination with the evaporative nature of the volatile composition results in an odor intensity and length of life which supports the intended purpose of the membrane device. Accordingly, the width of the perimeter seam (16) can be adjusted during the manufacturing process to accommodate the amount of volatile composition required for various embodiments of the membrane device. By adjusting the seaming widths of the membrane device (15), the internal void volume of the fill zone that contains the volatile composition can be reduced. For example, as shown in FIG. 3B, the perimeter seam (16) can be widened so as to close off excessive void volume in the fill zone of the membrane device when a lesser amount of the volatile composition is needed for a particular application. In addition, appropriate adjustment of the seaming widths can orient the fill zone so that the volatile composition is positioned directly beneath the vapor releasing membrane (20). This assures maximum contact between the volatile composition intended for release and the vapor permeable membrane (20) and avoids the potential for the volatile composition to collect in areas of the membrane device (15) which are not readily exposed to the vapor releasing membrane (20).

Tear Strip

The membrane device (15) also includes a tear strip comprising a removable segment (23) and a tear strip handle (17). The removable segment can be positioned over the window (19) of the upper barrier panel. The removable segment can be the portion of the upper barrier panel (18A) that was removed to form the window (19). The segment (23) can be positioned in such a way that it can be re-positioned exactly over the window (19) from which it was removed.

The removable segment (23) is positioned beneath a sealing tear strip handle (17). The tear strip handle includes an adhesive coated side (22). The removable segment (23) can be attached to the adhesive coated side (22) of the sealing tear strip handle (17) such that the removable segment can be removed when the tear strip handle is removed. The tear strip handle (17) can be designed such that the removable segment (23), when properly affixed thereto, is in position to orient perfectly over the die cut window (19). The removable segment (23) and tear strip handle (17) engage with the upper barrier panel (18A) to create a closure to the membrane device and prevent unwanted loss of the volatile medium when the membrane device is not in use. While an embodiment of the tear strip including both a removable segment and a tear strip handle is described herein, those having ordinary skill in the art will understand that other configurations can be used without departing from the scope of the disclosed subject matter as long as the tear strip prevents exposure of the vapor releasing membrane to the surrounding environment until the tear strip is removed. For example, in accordance with an embodiment of the disclosed subject matter, the tear strip handle can be formed integrally with the removable segment.

Use of a removable segment (23) to cover the window (19) from which the removable segment was die cut can add to the sealing effectiveness of the tear strip and can provide a barrier between the vapor permeable membrane (20) and the adhesive composition on the sealing tear strip. The potential for unwanted interaction between the vapor emanating from the release membrane (20) and the adhesive coating on the sealing tear strip is of serious concern. The re-use and positioning of this barrier panel segment (23) directly over the window (19) from which it was removed significantly reduces the likelihood for these negative interactions.

With further reference to FIG. 3A, the partial removal of the tear strip from the membrane device (15) in accordance with one embodiment of the disclosed subject matter is shown. The sealing tear strip can be separated from the upper barrier panel (18A) to expose the die cut window (19) in the upper barrier panel, which results in the exposure of the vapor releasing membrane (20) and release of the volatile composition (21). The removable segment (23) remains attached to the adhesive coated side (22) of the sealing tear strip handle (17).

FIG. 4 depicts an exterior perspective view of the membrane device (15) of FIG. 3A in which the attached sealing tear strip has been completely separated from the upper barrier panel (18A), thus fully exposing the full length and width of the vapor permeable membrane (20) volatile composition (21) contained within the membrane device (15).

FIG. 4 also shows the upper barrier panel (18A) including side panels (24) that surround the vapor permeable membrane (20). The side panels (24) can be provided with some type of graphic enhancement. This added option for a design aesthetic allows the membrane device to serve both a functional (i.e., vapor-releasing) and aesthetic purpose. The printable surfaces of the side panels can allow for use of color graphics or other design elements which contribute to the aesthetic character of the membrane device, and which have been absent in the previously-proposed membrane devices.

Pouch Configuration

Figure 9:
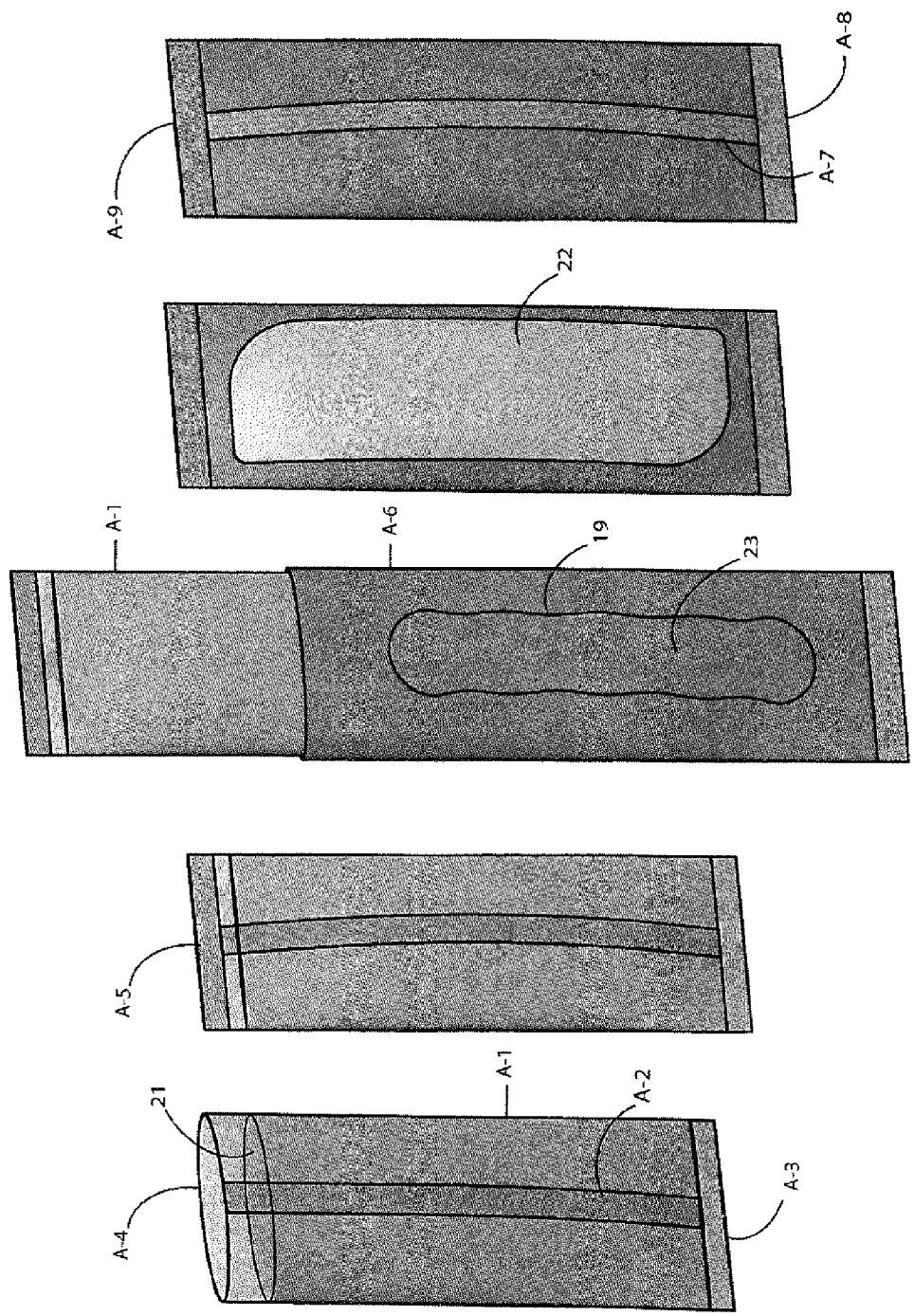
FIG. 9 illustrates five exterior perspective views of a filled, sealed and printed membrane device in accordance with one embodiment of the disclosed subject matter.
Figure 10:
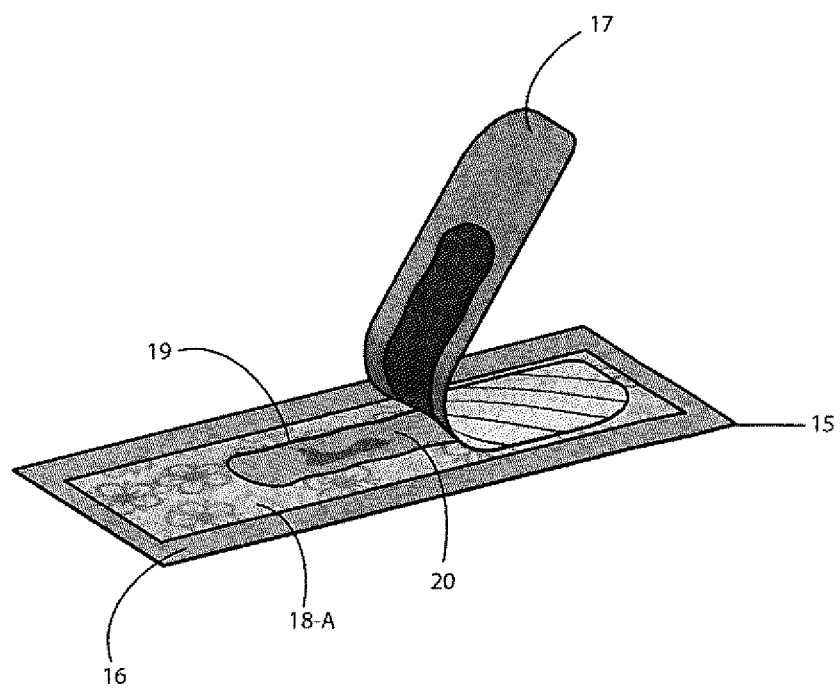
FIG. 10 illustrates an exterior perspective view of a membrane device having the same outside dimensions as the membrane device illustrated in FIG. 8, but with a substantially smaller window than that shown in FIG. 8.

In accordance with another embodiment of the disclosed subject matter, the membrane device can be fabricated in a pouch configuration. With reference to FIG. 9, the membrane device includes an inner pouch (A-1) and an outer pouch (A-6).

The inner pouch (A-1) acts as the vapor releasing membrane, and can be formed from the same materials as described above with respect to the vapor releasing membrane (20) of FIG. 2. The vapor permeable material can be formed into a pouch using a fin seal (A-2) that runs down the back spine of the pouch (A-1). The inner pouch can also include a cross seam (A-3) at one end of the pouch (A-1). The volatile medium is inserted into the open end of the pouch (A-4). The inner pouch (A-1) can then be sealed to form a cross seam (A-5). The pouch can be sealed using a heat seal, a sonic weld, or using any other sealing technique as known in the art for its intended purpose.

The inner pouch (A-1) can then be inserted into the outer pouch (A-6). Alternatively, the outer pouch (A-6) can be formed around the inner pouch (A-1). The outer pouch (A-6) is fabricated using vapor impermeable materials. A die cut segment (23) can be formed in the outer pouch (A-6). However, other techniques (e.g., a kiss-cut) can be used to faun the die-cut window (19).

A tear strip (22) can then be placed over the die cut segment so as to completely cover the die cut window (19). The tear strip (22), when actuated, will remove the die cut segment (23) and activate the dispersal of the volatile medium from the inner pouch (A-1).

The outer pouch (A-6) can be formed by a fin seal (A-7) and cross seams (A-8 and A-9).

In another embodiment of the disclosed subject matter, the inner pouch can be formed by sealing a volatile composition between two sheets of vapor permeable material, e.g., in a four-seam configuration, or between one sheet of vapor permeable material and one sheet of vapor impermeable material. Similarly, the outer pouch can be formed by sealing together an upper barrier panel of vapor impermeable material and a lower barrier panel of vapor impermeable material.

Dispersion

Figure 11:
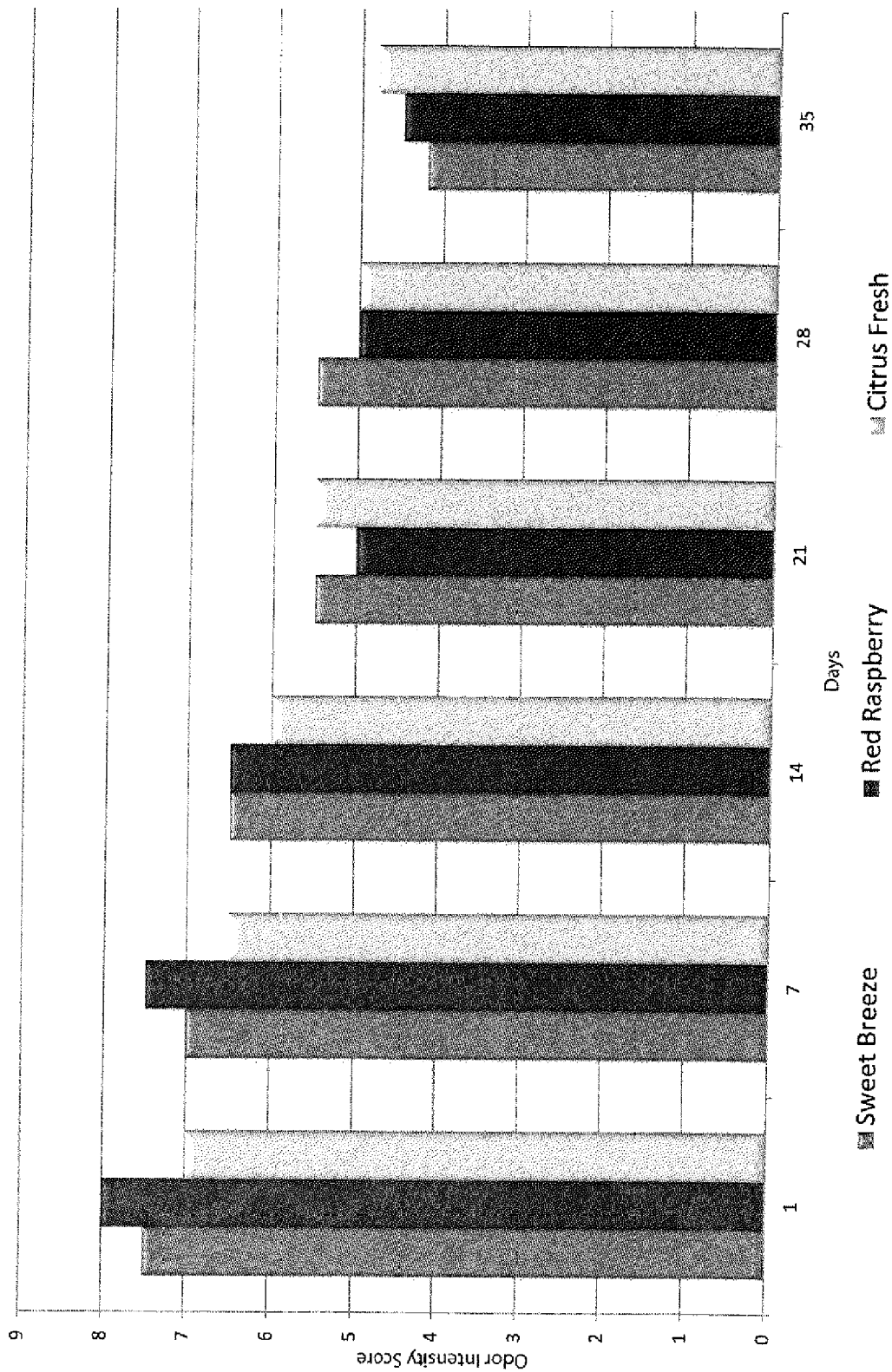
FIG. 11 illustrates a chart showing odor intensity score generated by dispersal of three fragrances using a membrane device in accordance with one embodiment of the disclosed subject matter as judged by an expert panel over the course of 35 days.

The membrane devices in accordance with the disclosed subject matter show consistent dispersion patterns. For example, FIG. 11 shows a chart of odor intensity score of three fragrances obtained over the course of 35 days by an expert panel. Fragrances were evaluated for intensity on a 10 point scale. Units being evaluated contained membranes with a thickness of 0.0025 inches, had an exposed membrane surface of 2.33 in$^2$, and contained 3.5 grams of fragrance oil. All units were tested in a 800 ft$^3$ odor evaluation room.

Figure 12:
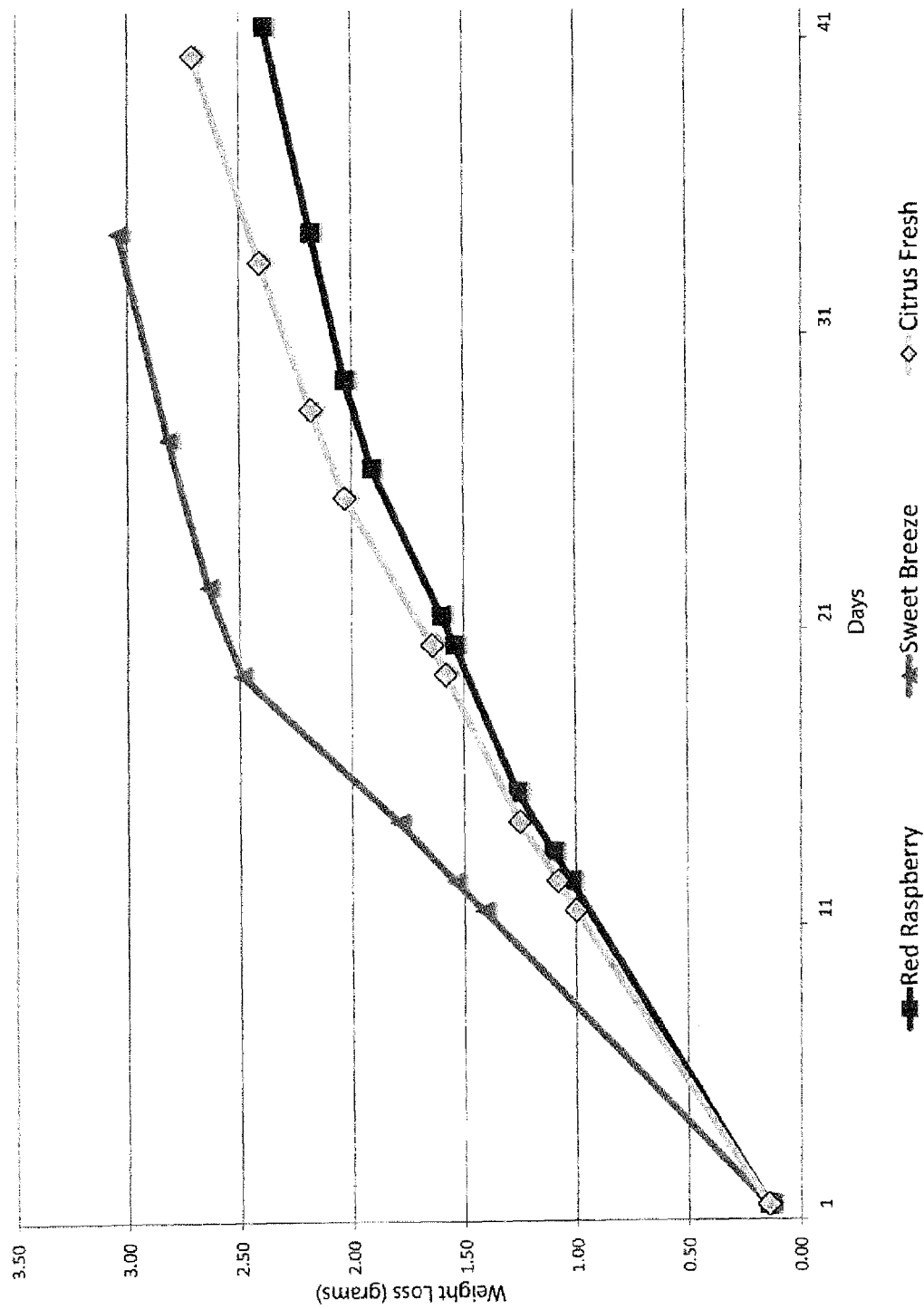
FIG. 12 illustrates total weight loss of volatile medium in membrane devices in accordance with one embodiment of the disclosed subject matter over time.

FIG. 12 shows a chart of how much of the volatile medium is being used over time. In particular, FIG. 12 illustrates total weight loss as a result of fragrance evaporation for three membrane units containing different fragrances. Units being evaluated contained membranes with a thickness of 0.0035 inches, had an exposed membrane surface of 2.33 in$^2$, and contained 3.5 grams of fragrance oil. All units were tested in a 800 ft$^3$ odor evaluation room.

Methods of Use

The disclosed subject matter thus provides a flexibly constructed multi-layered membrane device (15) intended for the release of volatile compositions. The compact execution of the membrane device (15) allows for easy replacement, shipping and handling and storage of the membrane device. The flexible and compact nature of this package also permits the user to place the device wherever an improved olfactive experience is desired without the need to be concerned about accidental spillage or breakage, or proximity to an electrical outlet. The membrane device can also be fabricated such that its size can be adjusted without requiring major changes to the manufacturing line when alternate sized membrane devices are needed for various applications. In this way, significant expenses associated with manufacturing line changes can be avoided while still permitting the option of varying the size of the membrane device to suit the needs of a particular application.

The inexpensive materials used in forming the disclosed flexible device along with the ability to make large volumes of membrane devices in short periods of time on available web converting machine lines make this a very cost effective and disposable device. Moreover, the depletion of the volatile composition over the course of the functional life of the membrane device results in a visibly empty package and therefore provides a visual indication to the user that the membrane device is depleted. A further benefit of the disclosed subject is that, in contrast to air freshening options that use large amounts of injection molded plastic or require metals cans to form or disperse their product, the disclosed membrane devices do not contribute excess waste when the unit is depleted.

Typical locations where the membrane devices can be placed include drawers, refuse receptacles, heating vents or registers, bathrooms, closets, gym bags, cars/automobiles, and the like. An adhesive placement strip can be provided on the membrane device. For example, an adhesive placement strip can be attached to the outer surface of the lower barrier panel. The adhesive placement strip allows a user to attach the membrane device to any flat surface for convenient placement. The membrane device can be positioned, for example, beneath a surface such that the membrane device is completely concealed from view when in use.

The membrane device in accordance with the disclosed subject matter can also be used as a fabric refresher. The release of a volatile fragrance composition for the purposes of enhancing the odor in a closed space as previously described would also prove to be a benefit if the membrane device were used in the confines of a laundry dryer. The release of the fragrance during the heated dryer cycle encountered during the process of cleaning clothing would have a significant benefit in imparting a pleasant odor to freshly washed laundry. The ability of the membrane device to be readily modified, so as to control the release of the volatile composition when exposed to the elevated temperatures encountered in the dryer cycle of the clothes drying process, makes it uniquely well-suited for this application. Decreasing the size of the window can provide membrane devices that are well-suited for dryer use as compared to those units designed for ambient temperature conditions meant for use in room air freshening applications. Increasing the thickness of the membrane can also contribute to retarding the vapor release from the unit when used in those elevated temperature conditions, like those that are likely to be found in the heated drying cycle of a home or commercial laundry dryer. The membrane device can also be sized in such a way that a single membrane device can be used on multiple dryer loads before the volatile composition is depleted, increasing the economic efficiency of the membrane device.

Laundry is commonly fragranced by using fragrance compositions added to the products intended for the wash cycle which become deposited onto the fabric and have to withstand the wash and rinse cycles, in order to pass through to the dryer cycle. In contrast, the use of a membrane device in accordance with the disclosed subject matter results in the fragrance being applied directly into the air in the dryer and indirectly onto the fabric to create a pleasant odor on the fabric. The opportunity of avoiding the wash cycle enables an expanded fragrance palette to be utilized. This will translate into the availability of a wider selection of fragrance types and the potential to create a more varied fragrance experience for the user.

Figures 5A, 5B:
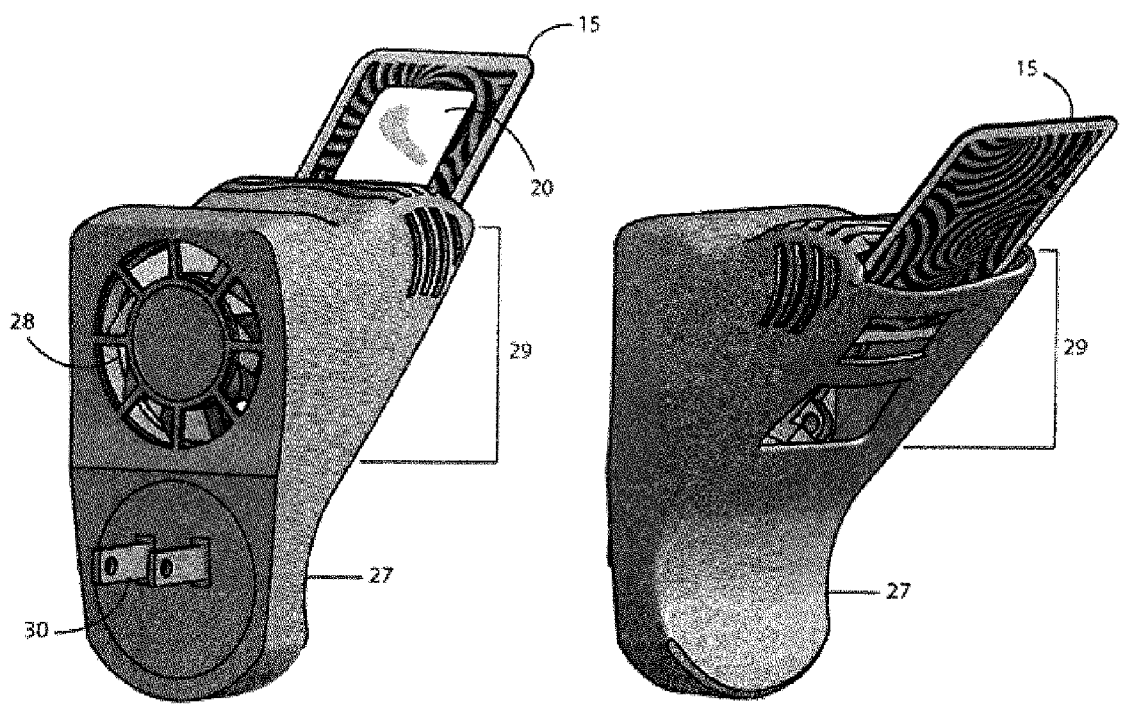
FIG. 5A illustrates a rear perspective view of a dispersal device including a housing incorporating an electrically driven fan and a membrane device in accordance with one embodiment of the disclosed subject matter. The membrane device is partially inserted into an upper chamber of the housing, which is designed to receive the membrane device.
FIG. 5B illustrates a partially rotated frontal view of the same dispersal unit depicted in FIG. 5A.

The membrane device in accordance with the disclosed subject matter can be used either as a stand-alone device or in combination with other elements. For example, FIG. 5A depicts a dispersal unit formed by a housing (27) including a fan (28) and a membrane device (15) in accordance with the disclosed subject matter. The fan (28) is operable to move air past the surface of the membrane device (15). The seal strip was removed from the membrane device (15) in FIG. 5A and the membrane device (15) was subsequently partially inserted into the holding chamber (29). The membrane unit (15) is oriented according to the configuration of the holding chamber (29). In FIG. 5A, the holding chamber (29) is integrated into the unit housing (27) such that the vapor releasing membrane (20) rests in an angular position relative to the fan. As such, the moving air deflects off the surface of the releasing membrane (20) and assists in moving the vapor released from the membrane device (15) into the surrounding atmosphere. The membrane device (15) is sized to fit into the holding chamber (29). Use of moving air is likely to permit the use of a smaller membrane device than those sized to work under static conditions.

FIG. 5A also shows the electrical prongs (30) on the housing (27) which are suitable for insertion into an electrical source to power the fan.

Figure 5C:
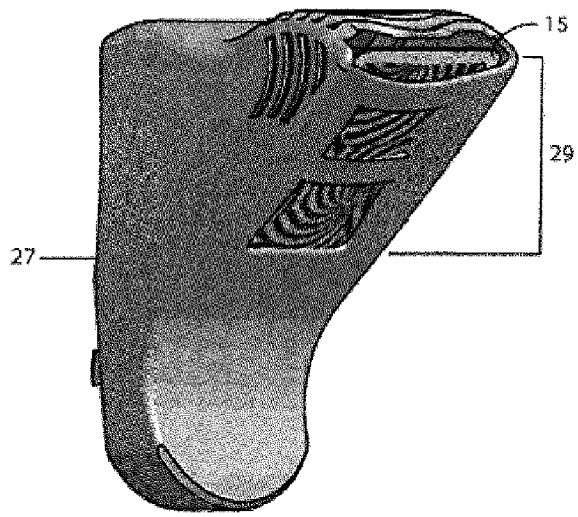
FIG. 5C illustrates a partially rotated frontal view of the dispersal unit depicted in FIG. 5A. The membrane device in FIG. 5C has been fully inserted into the housing and appears as it would in an operational mode

FIG. 5B shows a partially rotated frontal elevation view of the dispersal unit of FIG. 5A, again with the membrane device (15) partially inserted into the holding chamber (29). The membrane device (15) rests at an angular orientation in relation to the fan (28). The angle of orientation is meant to maximize the exposure of the vapor releasing membrane (20) to the accelerated air coming from the fan (28). The holding chamber (29) includes vented openings so as to allow for the free passage of the volatile composition of the membrane device to be forcibly carried by the accelerated air into the surrounding atmosphere FIG. 5C shows the dispersal unit depicted in FIGS. 5A and 5B with the membrane device (15) fully inserted into the holding chamber (29). FIG. 5C therefore illustrates the appearance of the dispersal unit in a fully operational mode.

In accordance with another embodiment of the disclosed subject matter, a heating element can be used instead of or in addition to the fan to assist in the dispersion process.

Figures 6A, 6B:
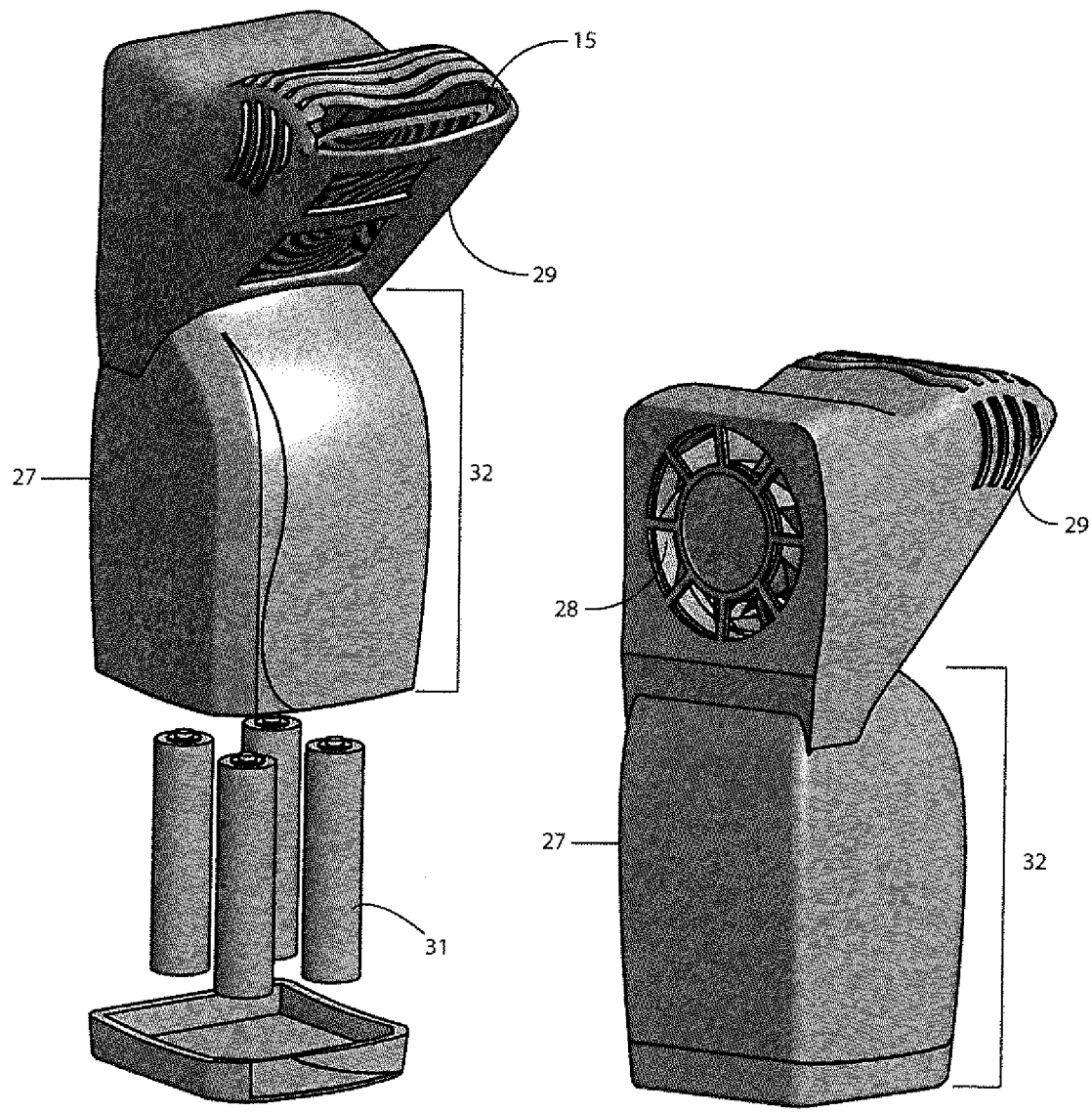
FIG. 6A illustrates a partially exploded frontal perspective view of a dispersal unit including a housing incorporating a fan and a battery pack. A membrane device in accordance with one embodiment of the disclosed subject matter is fully inserted into an upper chamber of the housing.
FIG. 6B illustrates a rear perspective view of an assembled dispersal unit including a housing incorporating an electrically driven fan and a battery pack. The housing contains a membrane device in accordance with one embodiment of the disclosed subject matter.

FIG. 6A depicts another embodiment of a dispersal unit, wherein the housing (27) includes a fan (28) and a membrane device (15). When operational, the fan moves air past the surface of the membrane device (15) as previously described with reference to FIG. 5A. The membrane device of FIG. 6A is fully activated as the seal strip has been removed and the membrane device is fully inserted in the holding chamber (29). The housing (27) also includes battery pack (31). In this embodiment, the energy required to drive the fan is satisfied through the use of a battery array. A person having ordinary skill in the art will understand that other energy sources can also be used to power the fan. The battery pack housing (32) can also create a different unit profile. Use of a battery pack can provide additional flexibility because the membrane device (15) can be used in areas not in proximity to an electrical outlet.

FIG. 6B is a rear perspective of the unit depicted in FIG. 6A. The dispersal unit includes a fan (28) and a battery pack that is fully encased by a portion of the housing (32) designed for that purpose. FIG. 6B illustrates the appearance of the dispersal unit in a fully operational mode.

The use of an energy-powered device also provides additional options for circuit design or programming. For example, the device dispersal unit can include an electrical circuit which allows for intermittent operation of the fan. In another embodiment, the dispersal unit can be programmed to run the fan in certain periods of the day or night. The dispersal unit can also include a motion detector or light sensing photo cell or timer. These components can be used to control when the fan should be operational. Intermittent use of the fan can prolong the life of the dispersal unit and keep the performance of the dispersal unit optimized around those periods of the day when someone is most likely to notice the fragrance.

The dispersal unit can also include a heating element. The heating element can be located in the holding chamber and can be placed in close proximity to the membrane device to accelerate the vapor permeation through the membrane and ultimate dispersion into the atmosphere. The heating element can also be used in conjunction with a fan which would force the vapor released from the membrane device to be more quickly expelled into the surrounding atmosphere. This would decrease the membrane device's reliance on convection currents for fragrance dispersion.

While the present application is described herein in terms of certain preferred embodiments, those skilled in the art will recognize that various modifications and improvements can be made to the application without departing from the scope thereof. Thus, it is intended that the present application include modifications and improvements that are within the scope of the appended claims and their improvements. Moreover, although individual features of one embodiment of the application may be discussed herein or shown in the drawings of one embodiment and not in other embodiments, it should be apparent that individual features of one embodiment can be combined with one or more features of another embodiment or features from a plurality of embodiments.

In addition to the specific embodiments claimed below, the application is also directed to other embodiments having any other possible combination of the dependent features claimed below and those claimed above. As such, the particular features presented in the dependent claims and disclosed above can be combined with each other in other manners within the scope of the application such that the application should be recognized as also specifically directed to other embodiments having any other possible combinations. Thus, the foregoing description of specific embodiments of the application has been presented for purposes of illustration and description. It is not intended to be exhaustive or to limit the application to those embodiments disclosed.

What is claimed is:

1. A membrane device for release of a volatile composition, the membrane device comprising:
    a lower barrier panel comprising an impermeable material;
    an upper barrier panel comprising a plurality of layers that form an impermeable continuous material, wherein the upper barrier panel includes a removable segment and a window having a perimeter formed by an uncut portion of the plurality of layers;
    a membrane layer comprising a permeable material, the membrane layer being sealed between the lower barrier panel and the upper barrier panel;
    a design element printed on an outer layer of the upper barrier panel, wherein separation of the removable segment from the membrane device exposes side panels of the upper barrier panel formed by the window that have the design element printed thereon, wherein the side panels surround the membrane layer;
    a volatile composition initially located in a fill zone formed in a void volume between the lower barrier panel and the membrane layer and sealed between the lower barrier panel and the membrane layer, wherein volatile composition is diffused through membrane layer when the membrane device is activated; and
    a tear strip handle attached to the removable segment, wherein the tear strip handle separates the removable segment of the upper barrier panel from the membrane device along the perimeter at the uncut portion to expose the membrane layer to release the volatile composition.

2. The membrane device of claim 1, wherein the volatile composition comprises at least one of a fragrance, a liquid, and a gel.

3. The membrane device of claim 1, wherein the tear strip handle is bonded to the upper barrier panel on an adhesive-coated side thereof.

4. The membrane device of claim 1, wherein the uncut portion defining the window is formed from at least one of a kiss-cut and a die-cut.

5. The membrane device of claim 1, wherein one of the plurality of layers of the upper barrier panel comprises a vapor impermeable layer.

6. The membrane device of claim 5, wherein one of the plurality of layers of the upper barrier panel comprises a sealing layer.

7. The membrane device of claim 1, further comprising an adhesive placement strip attached to an outer portion of the membrane device.

8. A method of releasing a volatile composition from a membrane device, comprising:
    providing a membrane device comprising:
        a lower barrier panel comprising an impermeable material;
        an upper barrier panel comprising a plurality of layers that form an impermeable continuous material, wherein the upper barrier panel includes a removable segment and a window having a perimeter formed by an uncut portion of the plurality of layers;
        a design element printed on an outer layer of the upper barrier panel;
        a membrane layer comprising a permeable material, the membrane layer being sealed between the lower barrier panel and the upper barrier panel;
        a volatile composition initially located in a fill zone formed in a void volume between the lower barrier panel and the membrane layer and sealed between the lower barrier panel and the membrane layer, wherein volatile composition is diffused through membrane layer when the membrane device is activated; and
        a tear strip handle attached to the removable segment; and
    removing the removable segment of the upper barrier panel along the perimeter at the uncut portion to expose and activate the membrane layer to release the volatile composition by applying a force to the tear strip handle, wherein separation of the removable segment from the membrane device exposes side panels of the upper barrier panel formed by the window that have the design element printed thereon, wherein the side panels surround the membrane layer.

9. The method of claim 8, further comprising placing the membrane device using an adhesive placement strip.

10. The method of claim 9, wherein the membrane device is placed beneath a surface.

11. The method of claim 8, further comprising placing the membrane device in a laundry dryer.

12. The method of claim 8, further comprising placing the membrane device in a dispersal unit.

13. The method of claim 12, further comprising activating a fan of the dispersal unit.

14. The method of claim 12, further comprising activating a heating element of the dispersal unit.

15. The membrane device of claim 1, wherein the upper barrier panel has a thickness dimension and the uncut portion has a thickness dimension, wherein the thickness dimension of the uncut portion is less than the thickness dimension of the upper barrier panel.

16. The membrane device of claim 15, wherein the thickness dimension of the upper barrier panel ranges and includes between about 3 mils to about 5 mils.

17. The membrane device of claim 1, wherein a surface area of the removable segment depends on a desired release rate of the volatile composition.

18. The membrane device of claim 1, wherein the plurality of layers of the upper barrier panel includes a sealing layer, a vapor impermeable layer, and an outer layer, wherein the vapor impermeable layer is positioned between the sealing layer and the outer layer.

19. The membrane device of claim 1, wherein the window is formed in an outer layer of the upper barrier panel.

20. The method of claim 8, wherein the upper barrier panel has a thickness dimension and the uncut portion has a thickness dimension, wherein the thickness dimension of the uncut portion is less than the thickness dimension of the upper barrier panel.

* * * * *